US005109019A

United States Patent [19]

Lehmann et al.

[11] Patent Number: 5,109,019

[45] Date of Patent: Apr. 28, 1992

[54] FUNGICIDAL MIXTURES

[75] Inventors: Rudolf Lehmann, Leichlingen; Hans T. Leinen, Duesseldorf; Reinhard Orth, Monheim; Hans-Juergen Mueller, Duesseldorf, all of Fed. Rep. of Germany

[73] Assignee: Henkel Kommanditgesellschaft auf Aktien, Duesseldorf, Fed. Rep. of Germany

[21] Appl. No.: 376,976

[22] Filed: Jul. 6, 1989

Related U.S. Application Data

[63] Continuation of Ser. No. 202,842, Jun. 3, 1988, abandoned.

[30] Foreign Application Priority Data

Jun. 9, 1987 [DE] Fed. Rep. of Germany ....... 3719194

[51] Int. Cl.[5] ...................... A01N 47/10; A01N 33/12
[52] U.S. Cl. .................................... 514/479; 514/643
[58] Field of Search ................ 514/642, 643, 478, 479

[56] References Cited

U.S. PATENT DOCUMENTS

| | | | |
|---|---|---|---|
| 3,054,678 | 9/1962 | Michner et al. .................... | 514/642 |
| 4,474,807 | 10/1984 | Gerhardt et al. .................. | 514/478 |

FOREIGN PATENT DOCUMENTS

| | | | |
|---|---|---|---|
| 0093962 | 6/1982 | European Pat. Off. . | |
| 0093963 | 6/1982 | European Pat. Off. . | |
| 0189844 | 6/1986 | European Pat. Off. . | |
| 3116894 | 11/1983 | Fed. Rep. of Germany . | |
| 3216895 | 11/1983 | Fed. Rep. of Germany . | |
| 2169511 | 7/1986 | United Kingdom ................ | 514/642 |

OTHER PUBLICATIONS

Kirk-Othmer Encyclopedia of Chemical Technology, Third Edition, vol. 19, 1982, p. 530.
Tenside-Textilhilfsmittel-Waschrohstoffe, Dr. Kurt Lindner, 1964, p. 984.

*Primary Examiner*—Frederick Waddell
*Assistant Examiner*—Zohreh A. Fay
*Attorney, Agent, or Firm*—Ernest J. Szoke; Wayne C. Jaeschke; Henry E. Millson, Jr.

[57] ABSTRACT

Antimicrobial mixtures containing quaternary ammonium compounds and iodopropynyloxy ethanol carbamate compounds in a ratio by weight of 0.3:1 to 9:1.

18 Claims, No Drawings

FUNGICIDAL MIXTURES

This application is a continuation of application Ser. No. 07/202,842, filed Jun. 3, 1988, now abandoned.

BACKGROUND OF THE INVENTION

1. Field of the Invention

This invention relates to fungicidal mixtures, more especially antimicrobial mixtures, containing quaternary ammonium compounds and iodopropynyloxy ethanol carbamate compounds.

2. Statement of Related Art

The use of quaternary ammonium halides as active components in antimicrobial preparations has long been known, see for example K. Lindner, Tenside-Textilhilfsmittel-Waschrohstoffe, 2nd Edition, Vol. 1, Wissenschaftliche Verlagsgesellschaft mbH, Stuttgart 1964, page 984 and Kirk-Othmer, Encyclopedia of Chemical Technology, 3rd Edition, Volume 19, John Wiley & Sons, New York/Chichester/Brisbane/Toronto/Singapore 1982, page 530. The use of iodopropynyloxy ethanol carbamates as bactericides and fungicides has also been known for some time, see for example German Application No. 32 16 895 A1.

In the field of disinfectants and preservatives, there is a need, both on environmental and on economic grounds, for active substances and combinations of active substances which develop adequate antimicrobial activity in low in-use concentrations. In this connection, not only new compounds, but also synergistic combinations of already know active substances are of interest.

DESCRIPTION OF THE INVENTION

Other than in the operating examples, or where otherwise indicated, all numbers expressing quantities of ingredients or reaction conditions used herein are to be understood as modified in all instances by the term "about".

It has now been found that combinations of quaternary ammonium halides of the benzalkone type and iodopropynyloxy ethanol carbamates show synergistic antimicrobial activity when the two components are present in certain weight ratios.

More particularly, the present invention relates to antimicrobial mixtures containing a) at least one antimicrobial quaternary ammonium compound, and b) at least one antimicrobial iodopropynyloxy ethanol carbamate compound, wherein components a) and b) are present in a ratio by weight of a to b of 0.3:1 to 9:1.

The component a) antimicrobial quaternary ammonium compounds are compounds of the benzalkone type which correspond to the following formula $$[R^1R^2N^{\oplus}(CH_3)_2]X^{\ominus} \quad (I)$$

in which $R^1$ and $R^2$ can be the same or different and represent a preferably linear $C_8$–$C_{18}$ alkyl radical or a benzyl radical and $X^{\ominus}$ is a halide anion, e.g., chloride, bromide or iodide, and more especially a chloride anion; and wherein only one of the substituents $R^1$ or $R^2$ is a benzyl radical. These quaternary ammonium compounds can be present in the mixtures of the invention as single compounds of formula I or as mixtures of two or more such compounds. Examples of antimicrobial quaternary ammonium compounds of this type are benzyldimethyl-n-decylammonium chloride; benzyldimethyl-n-dodecylammonium chloride; benzyldimethyl-n-tetradecylammonium chloride; benzyldimethyl-n-octadecylammonium chloride; benzyldiethyl coconut alkyl ammonium chloride, in which the substituent $R^1$ in formula I is derived from the hydrogenated fatty acid mixture of coconut oil; dioctyldimethylammonium chloride; and didecyldimethylammonium chloride. Benzyldimethyl-n-dodecylammonium chloride, benzyldimethyl-n-tetradecylammonium chloride, and mixtures of these compounds are preferred.

The component b) antimicrobial iodopropynyloxy ethanol carbamate compounds are 2-(3-iodo-2-propynyloxy)ethanol carbamates corresponding to the following general formula

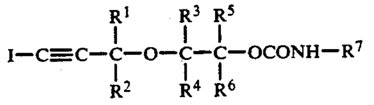
(II)

in which $R^1$ and $R^2$ can be the same or different and represent hydrogen, a linear or branched $C_1$–$C_6$ alkyl or alkenyl radical, or a cyclic $C_5$–$C_7$ alkyl radical, or $R^1$ and $R^2$ together represent $-(CH_2)_n-$ with $n=4$ to 6, $R^3$, $R^4$, $R^5$ and $R^6$ can be the same or different and represent hydrogen, a $C_1$–$C_4$ alkyl radical, an aryl radical, $-CCl_3$, or $R^3$ and $R^5$ or $R^4$ and $R^6$ together represent $-(CH_2)_m-$ with $m=3$ to 5, and $R^7$ is hydrogen, a linear or branched $C_1$–$C_{12}$ alkyl radical, a cyclic aryl radical, an aralkyl radical, or an arylsufonyl radical.

Examples of linear or branched $C_1$–$C_6$ alkyl or alkenyl radicals, as represented by $R^1$ and $R^2$, include methyl, ethyl, propyl, isopropyl, n-butyl, isobutyl, sec.-butyl, tert.-butyl, pentyl, hexyl and branched isomers thereof, vinyl, allyl, propenyl, butenyl, pentenyl and hexenyl, and also the corresponding isomers of the above alkenyl radicals containing 4, 5 and 6 carbon atoms. Examples of cyclic $C_5$–$C_7$ alkyl radicals, as represented by $R^1$ and $R^2$, include cyclopentane, cyclohexane, and cycloheptane. Preferred are compounds of formula (II) in which the substituents $R^1$ and $R^2$ are both either hydrogen or methyl, and to those compounds of formula (II) in which one of the substituents $R^1$ and $R^2$ is hydrogen and the other is methyl.

Examples of $C_1$–$C_4$ alkyl radicals, as represented by $R^3$, $R^4$, $R^5$ and $R^6$, include methyl, ethyl, propyl, isopropyl, n-butyl, isobutyl, sec.-butyl, and tert.-butyl, preferably methyl.

Examples of aryl radicals, as represented by $R^3$, $R^4$, $R^5$ and $R^6$, include phenyl and naphthyl.

Preferred are compounds of general formula (II), in which at least four of the substituents $R^1$ to $R^6$ are hydrogen.

Examples of linear and branched $C_1$–$C_{12}$ alkyl radicals, as represented by $R^7$, include methyl, ethyl, propyl, isopropyl, n-butyl, isobutyl, sec.-butyl, tert.-butyl, pentyl, hexyl, heptyl, octyl, nonyl, decyl, undecyl, dodecyl, and also the branched isomers of the above alkyl radicals that contain 5 to 12 carbon atoms.

Examples of cyclic $C_4$–$C_8$ alkyl radicals, as represented by $R^7$, include cyclobutyl, cyclopentyl, cyclohexyl, cycloheptyl and cyclooctyl.

Examples of aryl and substituted aryl, as represented by $R^7$, include phenyl, naphthyl, tolyl, chlorophenyl, bromophenyl, fluorophenyl, dichlorophenyl and trichlorophenyl.

Examples of aralkyl and aryl sulfonyl, as represented by $R^7$, include phenyl $C_1$–$C_6$ alkyl (e.g. benzyl), and p-toluenesulfonyl.

Preferred are compounds in which $R^7$ is a $C_1$–$C_4$ alkyl radical, an aryl radical, or a chlorine or bromine-substituted aryl radical.

Examples of particularly preferred compounds are those in which $R^7$ is propyl, butyl, or phenyl.

The N-substituted 2-(3-iodo-2-propynyloxy)-ethanol carbamates corresponding to general formula (II) are prepared in known manner (Houben-Weyl, Methoden der Org. Chemie, Vol. 8, pages 141–144 (1952)) by reaction of equimolar quantities of the alcohols with suitable, for example commercially available, isocyanates, as described for example in German applications 32 16 894 A1, and 32 16 895 A1.

When the mixtures of the invention were tested for their microbistatic effect on various fungal cultures, distinct synergistic effects were obtained.

In one preferred embodiment of the invention, the ratio by weight of components a) and b) is between 1:1 and 6:1.

For the preparation of ready-to-use antimicrobial preparations, the antimicrobial mixtures of the invention are made available in the form of aqueous concentrates in which the total concentration of components a and b are between 3 and 50% by weight. In the aqueous ready-to-use antimicrobial preparations, which are used for disinfecting and pre-serving purposes, the total concentration of components a and b is generally between 0.005 and 5% by weight, based on the preparation as a whole.

In the most simple case, the ready-to-use antimicrobial mixtures consist of an aqueous solution in which the quaternary ammonium compound and the iodopropynyloxy ethanol carbamate compound are dissolved in the ratio indicated and in the concentration indicated. In the majority of cases, the mixtures intended for practical application contain other constituents of the type normally used which are selected according to the particular formulation and the particular application envisaged. In addition to water, suitable solvents for liquid preparations include mixtures of water and water-miscible organic solvents, for example ethanol, isopropanol, ethylene glycol, propylene glycol, ethyl ethylene glycol and propyl propylene glycol. Solutions such as these may readily be sprayed using either compressed air or a propellant of the type commonly used in the aerosol field for the production of sprays.

Where an additional cleaning effect is required in addition to the antimicrobial effect, the mixtures of the invention can contain surfactants, particularly nonionic surfactants. Examples of suitable surfactants include adducts of 4 to 40 and preferably 4 to 20 moles ethylene oxide with 1 mole fatty alcohol, alkylcyclohexanol, alkylphenol, fatty acid, fatty amine, fatty acid amide, or alkane sulfonamide. Of particular interest are adducts of 5 to 16 moles ethylene oxide with coconut fatty alcohols, tallow fatty alcohol, oleyl alcohol, a mixture of oleyl alcohol and cetyl alcohol, mono-, di- or trialkylphenols, or with monoalkylcyclohexanols containing 6 to 14 carbon atoms in the alkyl radicals. Mixed adducts of ethylene oxide and propylene oxide with the above compounds containing an active hydrogen atom can also be used. The above alkoxylation products can also be terminally blocked, for example by ether or acetal groups.

In addition, the mixtures of the invention can contain builders. Suitable builders include for example, alkali metal salts of gluconic acid, more especially sodium gluconate, the alkali metal salts of nitrilotriacetic acid, ethylenediamine tetraacetic acid, hydroxyethane diphosphonic acid, phosphonobutane tricarboxylic acid, lactic acid, citric acid, or tartaric acid. Other builders include the water-soluble salts of relatively high molecular weight polycarboxylic acids, for example polymers of maleic acid, itaconic acid, fumaric acid, or citraconic acid. Copolymers of these acids with one another or with other polymerizable monomers, such as for example ethylene, propylene, acrylic acid, vinyl acetate, isobutylene, acrylamide, and styrene, can also be used.

The mixtures of the invention can also contain cleaning enchancers, such as fatty acid mono- and diethanolamides, for example cocnut fatty acid monoethanolamide and coconut fatty acid diethanolamide; adducts of up to 4 moles ethylene oxide or propylene oxide with $C_{12}$–$C_{18}$ alkylamines or $C_8$–$C_{12}$ fatty alcohols; free $C_8$–$C_{12}$ fatty alcohols; and cellulose-based cleaning enhancers.

In addition, it can be of advantage for further applications if the mixtures of the invention contain other antimicrobial agents in addition to the combination of quaternary ammonium compounds and iodopropynyloxy ethanol carbamate compounds.

In addition to liquid concentrates, solid products, preferably in powder or granulate form, which contain the antimicrobial mixtures of the invention, can also be used for the preparation of ready-to-use cleaning solutions having a disinfecting effect.

The synergistic antimicrobial mixtures of the invention can be used as disinfectants and preservatives in many fields, for example in surface disinfection in hospitals, schools, public baths, public transport, institutional buildings, and industrial plants. The mixtures of the invention are of particular importance in the field of disinfection in agriculture, in dairies and breweries and other branches of the food and beverage industry. In addition, the synergistic mixtures can be used for the preservation of plant propagation material, more especially seeds and bulbs. The mixtures of the invention can also be used in the preservation of other commercial products, such as dye dispersions, adhesives, drilling and cutting oils, or products of the type used in the paper-, cardboard- or leather-processing industry, and for the preservation of industrial water. Finally, the mixtures of the invention can be used in the protection of porous or semi-porous materials, for example for the impregnation of wood, e.g. to treat boxes of the type used in mushroom farming against attack by the culture mycelium.

The invention will be illustrated but not limited by the following examples.

EXAMPLES

EXAMPLE 1

The following aqueous solutions according to the invention (products C and D) were prepared from benzyldimethyl-n-dodecyl/n-tetradecylammonium chloride (70 mole % $C_{12}$; 30 mole % $C_{14}$; product A) and 2-(3-iodo-2-propynyloxy)-ethanol-N-ethyl carbamate (product B):

Product C (ratio A:B 4.5:1)

Product D (ratio A:B 1:1)

The microbistatic effect of the mixtures according to the invention (products C and D) by comparison with that of the individual components benzyldimethyl-n-dodecyl/n-tetradecylammonium chloride (A) and 2-(3-iodo-2-propynyloxy)-ethanol-N-ethyl carbamate (product B) was determined against the following test microorganism suspensions:

1. Candida albicans $1\times10^8$ microorganisms/ml
2. Penicillium camerunense $5\times10^7$ microorganisms/ml
3. Penicillium funiculosum $3\times10^7$ microorganisms/ml
4. Trichoderma viride $6\times10^7$ microorganisms/ml
5. Asperigillus niger $4\times10^7$ microorganisms/ml The inhibitory concentrations of the substances and mixtures of substances to be tested were determined in accordance with the "Richtlinien für die Prüfung und Bewertung chemischer Desinfektionsverfahren (Guidelines for the Testing and Evaluation of Chemical Disinfection Techniques)", Chapter 2.1 printed in Zbl. Bakt. Hyg. I Abt. Orig. B 172, 536-537 (1981). For all the test microorganisms, the concentrations of active substance (in ppm) were 20, 15, 10, 7, 4.5, 3, 2, 1.5 and 1. The concentration series was prepared in Würzebouillon.

The results obtained are shown in Table I below.

TABLE I

Inhibitory concentrations (in ppm) of products A to D

| Product | Test Microorganism 1 | 2 | 3 | 4 | 5 |
|---|---|---|---|---|---|
| A | 70 | 45 | 4.5 | 15 | 70 |
| B | 20 | 7 | 7 | 10 | 10 |
| C | 37 | 8.5 | 5.5 | 5.5 | 55 |
| D | 14 | 4 | 3 | 4 | 9 |

A synergistic effect was observed where products C and D according to the invention were used. In the context of the invention, the effect obtained is synergistic when, with a combination of both components, less than half the minimum inhibitory concentration (MIC) is required.

For the inhibitory concentrations of products C and D according to the invention, the Table shows the sum of the two individual components which were used in the ratios set forth above.

What is claimed is:

1. An antimicrobial mixture comprising
a) at least one antimicrobial quaternary ammonium compound of the formula $$(R^1R^2N^{(+)}(CH_3)_2)X^{(-)} \quad (I)$$

wherein $R^1$ and $R^2$ can be the same or different and represent a $C_8$-$C_{18}$ alkyl radical or a benzyl radical, provided that only one of $R^1$ and $R^2$ is a benzyl radical, and $X^{(-)}$ is a halide ion, and
b) at least one antimicrobial iodopropynyloxy ethanol carbamate compound of the formula

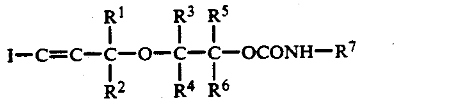

(II)

in which
$R^1$ and $R^2$ can be the same or different and represent hydrogen, a linear or branched $C_1$-$C_6$ alkyl or alkenyl radical, or a cyclic $C_5$-$C_7$ alkyl radical, or $R^1$ and $R^2$ together represent $-(CH_2)_n-$with n=4 to 6,
$R^3$, $R^4$, $R^5$ and $R^6$ can be the same or different and represent hydrogen, a $C_1$-$C_4$ alkyl radical, an aryl radical, $-CCl_3$, or $R^3$ and $R^5$ or $R^4$ and $R^6$ together represent $-(CH_2)_n-$with m=3 to 5, and
$R^7$ is hydrogen, a linear or branched $C_1$-$C_{12}$ alkyl radical, a cyclic $C_4$-$C_8$ alkyl radical, an aryl radical, a halogen- or $C_1$-$C_6$ alkyl-substituted aryl radical, an aralkyl radical, or an arylsulfonyl radical,
wherein components a) and b) are present in a ratio by weight of a) to b) of about 0.3:1 to 9:1.

2. The antimicrobial mixture of claim 1 wherein components a) and b) are present in a ratio by weight of a) to b) of about 1:1 to about 6:1.

3. The antimicrobial mixture of claim 1 wherein in component a) the $C_8$-$C_{18}$ alkyl radical is linear.

4. The antimicrobial mixture of claim 1 wherein in component a) $x^{(-)}$ is chloride.

5. The antimicrobial mixture of claim 1 wherein in component a) the at least one compound of formula I is benzyldimethyl-n-dodecylammonium chloride, benxyldimethyl-n-tetradecylammonium chloride, or a mixture thereof.

6. The antimicrobial mixture of claim 1 wherein in component b) the $R^1$ and $R^2$ groups in formula II are both hydrogen, both methyl, or one is hydrogen and the other methyl.

7. The antimicrobial mixture of claim 1 wherein in component b) at least four of the groups $R^1$ through $R^6$ are hydrogen.

8. The anticrobial mixture of claim 1 wherein in component b) $R^7$ is $C_1$-$C_4$ alkyl, aryl, or a chlorine or bromine-substituted aryl group.

9. The antimicrobial mixture of claim 8 wherein $R^7$ is propyl, butyl, or phenyl.

10. The antimicrobial mixture of claim 1 wherein the mixture is in the form of an aqueous concentrate wherein the total concentration of components a) and b) is from about 3 to about 50% by weight, based on the weight of the concentrate.

11. The antimicrobial mixture of claim 1 wherein the mixture is in the form of an aqueous solution in which the total concentration of components a) and b) is from about 0.005 to about 5% by weight, based on the weight of the aqueous solution.

12. A method of protecting a substance against microbial attack comprising treating the substance with an antimicrobial quantity of the mixture of claim 11.

13. A method of disinfecting an animal stall comprising treating the stall with a disinfecting quantity of the mixture of claim 11.

14. A method of disinfecting an animal stall comprising treating the stall with a disinfecting quantity of the mixture of claim 11.

15. A method of disinfecting a milking plant comprising treating the surfaces of the plant with a disinfecting quantity of the mixture of claim 11.

16. The method of claim 12 wherein the substance is wood.

17. The method of claim 12 wherein the substance is a plant propagation material.

18. An antimicrobial mixture comprising
a) benzyldimethyl-n-dodecyl/n-tetradecylammonium chloride, and
b) 2-(3-iodo-2-propynyloxy)-ethanol-n-ethyl carbamate; wherein components a) and b) are present in a ratio by weight of a) to b) of about 1:1 to about 4.5:1.

* * * * *